(12) United States Patent
Lee et al.

(10) Patent No.: US 6,924,078 B2
(45) Date of Patent: Aug. 2, 2005

(54) PHOTORESIST MONOMERS, POLYMERS AND PHOTORESIST COMPOSITIONS FOR PREVENTING ACID DIFFUSION

(75) Inventors: Geun Su Lee, Kyoungki-do (KR); Jae Chang Jung, Kyoungki-do (KR); Ki Soo Shin, Seoul (KR); Se Jin Choi, Seoul (KR); Deog Bae Kim, Seoul (KR); Jae Hyun Kim, Seoul (KR)

(73) Assignees: Hynix Semiconductor Inc., Kyoungki-Do (KR); Dongjin Semichem Co., Ltd., Inchon-Shi (KR)

( * ) Notice: Subject to any disclaimer, the term of this patent is extended or adjusted under 35 U.S.C. 154(b) by 0 days.

(21) Appl. No.: 10/225,992

(22) Filed: Aug. 22, 2002

(65) Prior Publication Data

US 2003/0091927 A1 May 15, 2003

(30) Foreign Application Priority Data

Aug. 24, 2001 (KR) ........................................ 2001-51442

(51) Int. Cl.$^7$ .............................. G03F 7/039; G03F 7/40
(52) U.S. Cl. ..................... 430/270.1; 430/311; 430/326; 430/296; 430/18; 430/942; 526/268; 526/281
(58) Field of Search ....................... 430/296, 18, 281.1, 430/282.1, 283.1, 284.1, 285.1, 286.1, 287.1, 288.1, 270.1, 311, 326; 526/268, 281

(56) References Cited

U.S. PATENT DOCUMENTS

| | | | |
|---|---|---|---|
| 3,557,062 A | * | 1/1971 | Vergne et al. ............... 526/281 |
| 4,607,110 A | * | 8/1986 | Herweh ....................... 526/268 |
| 4,766,187 A | * | 8/1988 | Beckley et al. ............. 526/209 |
| 4,997,899 A | | 3/1991 | Fujino |
| 5,081,307 A | | 1/1992 | Kitamura et al. |
| 5,786,125 A | | 7/1998 | Tsuchiya et al. |
| 6,013,412 A | | 1/2000 | Aoshima |
| 6,080,826 A | * | 6/2000 | Grubbs et al. ................ 526/75 |
| 6,124,077 A | | 9/2000 | Imai et al. |
| 6,177,230 B1 | | 1/2001 | Kawamura |
| 6,187,509 B1 | | 2/2001 | Imai et al. |
| 6,248,499 B1 | | 6/2001 | Maeda et al. |
| 6,303,724 B1 | * | 10/2001 | Goodall et al. ............. 526/266 |
| 6,316,162 B1 | | 11/2001 | Jung et al. |
| 2002/0015917 A1 | * | 2/2002 | Lee et al. ................. 430/270.1 |
| 2002/0098443 A1 | * | 7/2002 | Hatakeyama et al. .... 430/270.1 |
| 2003/0078354 A1 | * | 4/2003 | Medina et al. ........... 430/270.1 |

FOREIGN PATENT DOCUMENTS

| | | |
|---|---|---|
| JP | 08190193 A | 7/1996 |
| JP | 2000-191656 A | 7/2000 |

OTHER PUBLICATIONS

Vartanyan et al, Chemical Abstracts AN 92:58754 (6 pages from online and CD Chemical Abstracts), English abstract of Vartanyan et al, Aarmyanskii Khimisheskii Zhurnal (1979), 32(6), pp. 471–4 (in Russian), Copyright American Chemical Society 1999.*

Vartanian et al, Crown–Ether Chemistry, III. Synthesis of Cylci and Acyclic Polyethers Containing Double and Triple Bonds, Armyanskii Khimicheskii Zhurnal, vol. 32, No. 5, 1979, pp. 471–474, in Russian with English abstract.*

Taiwanese Official Letter dated Dec. 17, 2003 (3 pages).

T. Yamaaka et al., "Design of Photoresist Based on Diverse Reaction of Polyfunctional Vinyl Ether Monomers," Department of Information and Image Science, Chiba University, Chiba Japan, p. 55.

Geun Su Lee et al., "Macrocycle Monomer Having Ethyleneoxy Unit to Buffer Acid Diffusion (New Base for Photoresist)" Proceedings of SPIE vol. 4890 (2002) pp. 136–140.

\* cited by examiner

*Primary Examiner*—Cynthia Hamilton
(74) *Attorney, Agent, or Firm*—Marshall, Gerstein & Borun LLP

(57) ABSTRACT

Photoresist monomers, polymers thereof, photoresist compositions containing the same for preventing acid generated in the exposed area during the course of a photolithography process from being diffused to the unexposed area. The line edge roughness and slope pattern are improved when an ultrafine photoresist pattern is formed using photoresist copolymer having a multi-oxygen-containing compound as a repeating unit such as an ethyleneoxy moiety represented by Formula 1 with at least one polymerizable carbon-carbon double bond. In addition, the shape of pattern is improved by eliminating top loss and the adhesion of pattern to the substrate is improved.

Formula 1

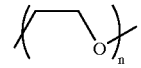

wherein n is an integer ranging from 1 to 5.

17 Claims, 4 Drawing Sheets

PHOTORESIST MONOMERS, POLYMERS AND PHOTORESIST COMPOSITIONS FOR PREVENTING ACID DIFFUSION

TECHNICAL FIELD

Photoresist monomers, polymers and photoresist compositions containing the same for preventing acid diffusion are disclosed. More specifically, photoresist monomers, polymers and photoresist compositions containing the same are disclosed that prevent acid generated in an exposed area during the course of a photolithography process from being diffused or migrating to the unexposed area. Also, processes for forming photoresist patterns using the above are also disclosed.

DESCRIPTION OF THE RELATED ART

Recently, in the manufacture of semiconductors, chemical amplification-type DUV (deep ultra violet) photoresists have proven to be useful in achieving high sensitivity in processes for forming ultrafine patterns. These photoresists are prepared by blending a photoacid generator with polymer matrix having acid labile structures.

According to the reaction mechanism of such a photoresist, the photoacid generator generates acid when it is irradiated by the light source, and the main chain or branched chain of the polymer matrix in the exposed portion reacts with the generated acid and is decomposed or cross-linked, so that the polarity of the polymer is considerably altered. This alteration of polarity results in a solubility difference in the developing solution between the exposed area and the unexposed area, thereby forming a positive or negative image of a mask on the substrate.

However, some of the acid generated in the exposed area is diffused to the unexposed area during the course of exposure or post exposure delay (PED) stage, so that the line edge roughness (LER) of the pattern is deteriorated and damage to the pattern such as top loss or slope is observed.

In order to prevent the acid diffusion described above, a weak basic amine or amide compound, which can react with the generated acid, has been conventionally added to a chemical amplification type photoresist composition to prevent the acid generated in the exposed area from diffusing or migrating to the unexposed area.

However, such an amine or amide compound has high light absorbance in the extremely short wave region of 250 nm or less, for example in the wavelength region of ArF (193 mn), which results in a deterioration of the sensitivity of a photoresist composition. Moreover, the LER is also deteriorated due to irregular diffusion of the above basic compounds.

SUMMARY OF THE DISCLOSURE

Accordingly, photoresist monomers comprising ethyleneoxy moiety and at least one polymerizable carbon-carbon double bond are disclosed which solves the aforenoted problems attributable to acid migration and/or the presence of amines or amides. Photoresist polymers comprising the above photoresist monomer are also disclosed.

Photoresist compositions comprising such photoresist polymers, which can prevent acid generated in the exposed area from being diffused to unexposed area are also disclosed.

Processes for forming an ultrafine pattern by using the above described photoresist composition are also disclosed.

Semiconductor devices produced by using the above described photoresist composition are also disclosed.

DETAILED DESCRIPTION OF THE PRESENTLY PREFERRED EMBODIMENTS

Figure 1:
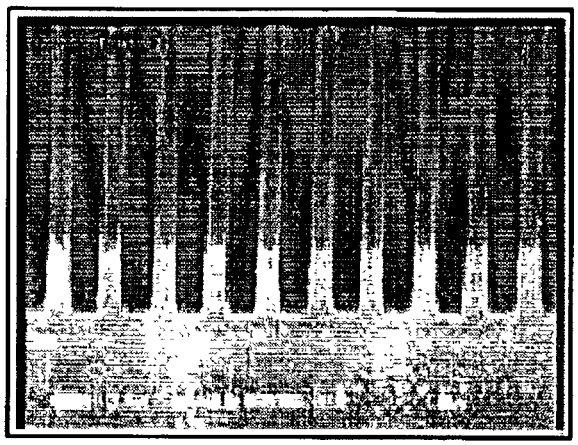
FIG. 1 is a photograph of a photoresist pattern obtained from Example 14.

Intensive studies have been performed to eliminate the acid migration or diffusion problem described above without resorting to the use of amines and amides. It has been found that the photoresist copolymers comprising multi-oxygen-containing compound which has at least one polymerizable carbon-carbon double bond and ethyleneoxy moiety are effective in preventing diffusion of acid generated in the course of exposure during the photolithography process.

Most oxygen-containing compounds such as ether have very weak basicity. However, as opposed to general ether compounds, crown ether compounds show strong basicity because several oxygens are regularly arranged in a crown ether molecule, and their lone electron pairs are concentrated in a narrow space to show a cooperative effect. In addition, multi-oxygen-containing compounds which comprise ethyleneoxy moiety have an excellent ability to transport acids or cations.

Thus, the multi-oxygen-containing compounds not only bind with acid in the unexposed area, but also transport and release the collected acid to the exposed area, thereby not decreasing the photosensitivity of the photoresist composition as opposed to using general basic compounds. Also, the photoresist itself has the ability of buffering and transporting the acid, thereby preventing surface damage of the pattern during the succeeding developing stage and decreasing the LER by inducing homogeneous diffusion of the acid.

At the same time, photoresist copolymers comprising repeating unit of multi-oxygen-containing compounds having ethyleneoxy moiety, in contrast to the conventional amine or amide compounds for preventing acid diffusion, have low light absorbance with extremely short wavelength of 250 nm or less. Therefore, the photosensitivity of a photoresist composition containing said photoresist copolymers is deteriorated.

In addition, as can be seen from the fact that multi-oxygen-containing compounds comprising ethyleneoxy moiety are used as phase-transfer catalysts between an organic layer and an aqueous layer, the disclosed photoresist compositions contribute to enhance contact between the organic layer and the aqueous layer. Thus, the LER is improved during developing stage and the adhesiveness of photoresist pattern to substrate can be enhanced by combining silicon oxide film with the disclosed photoresist compositions.

First, multi-oxygen-containing compounds comprising (i) ethyleneoxy moiety represented by Formula 1 and (ii) at least one polymerizable carbon-carbon double bond. It is used for photoresist monomer for preventing acid diffusion:

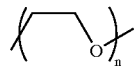

Formula 1 wherein, n is an integer from 1 to 5.

Any compound having at least one polymerizable carbon-carbon double bonds can be used for the moiety of the above monomer, such as vinylene derivatives or norbornene derivatives.

The above compounds are preferably selected from the group consisting of Formulas 2a to 2f:

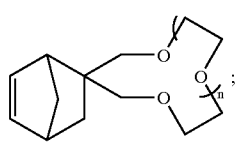

Formula 2a

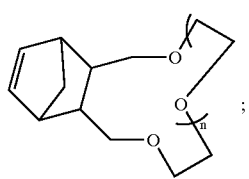

Formula 2b

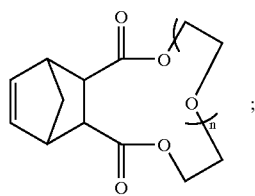

Formula 2c

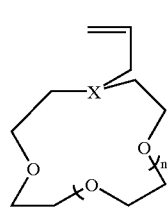

Formula 2d wherein, X is N or CH;

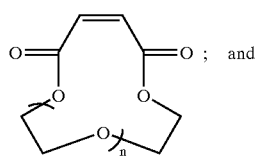

Formula 2e and

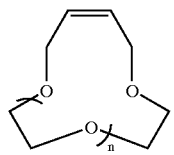

Formula 2f wherein, n is an integer ranging from 1 to 5.

Some of preferred above compounds are represented by Formulas 3a to 3f:

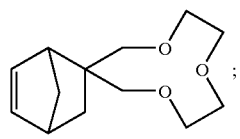

Formula 3a

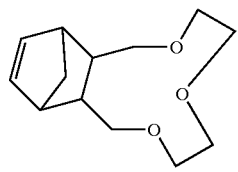

Formula 3b

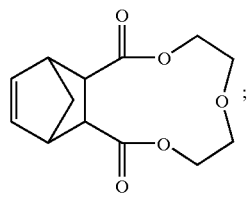

Formula 3c

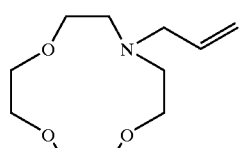

Formula 3d

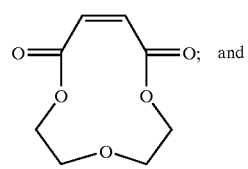

Formula 3e and

Formula 3f

In addition, photoresist copolymers are disclosed which comprise the multi-oxygen-containing compounds as mentioned above.

The above repeating units are preferably selected from the group consisting of Formulas 4a to 4f:

Formula 4a

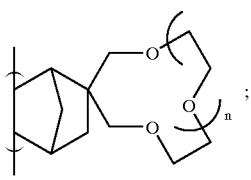

Formula 4b

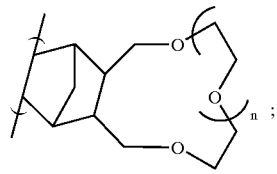

Formula 4c

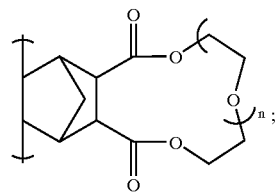

Formula 4d

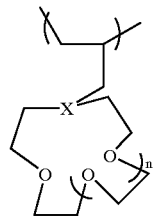

wherein, X is N or CH;

Formula 4e

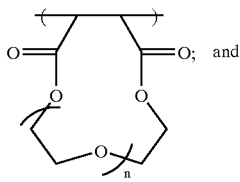
and

Formula 4f

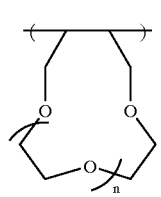

wherein, n is an integer ranging from 1 to 5.

The above repeating units of Formulas 4a to 4f are obtained through reactions with the double bonds of monomers of Formulas 2a to 2f independently during addition polymerization.

Some of preferred repeating units are represented by Formulas 5a to 5f:

Formula 5a

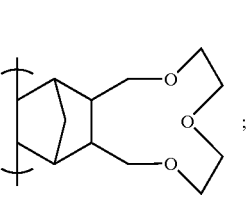

Formula 5b

Formula 5c

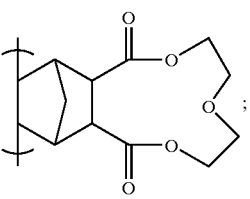

Formula 5d

[structure]

; and

Formula 5e

[structure]

Formula 5f

[structure]

The above repeating units of Formulas 5a to 5f are obtained by reactions with the double bonds of Formulas 3a to 3f independently during addition polymerization.

The multi-oxygen-containing compounds are used by being added as a base resin to a photo-amplification type photoresist resin such as KrF, i-line, ArF or VUV photoresist resin.

Some of base resins are disclosed in Korean Patent Application Nos. KR 97-26807, KR 97-77412, KR 97-81403, KR 98-34695, KR 99-16255 and KR 99-31299 filed by Hynix; or U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0 789 278 (Aug. 13, 1997), U.S. Pat. No. 6,132,926 (Oct. 17, 2000) and U.S. Pat. No. 6,180,316 B1 (Jan. 30, 2001).

The photoresist copolymer preferably comprises at least one repeating unit of Formula 6 or Formula 7 in order to inhibit dissolution of photoresist copolymer.

Formula 6

[structure with $R_3$, $R_4$, $A_2$, $B_2$, $k_2$, $R_1$, $R_2$, $X_1$, $Y_1$]

Formula 7

[structure with $R_6$, $R_5$, $R_7$]

wherein, $A_2$ and $B_2$ individually are selected from the group consisting of $CH_2$, $CH_2CH_2$, O and S;

$k_2$ is an integer ranging from 0 to 5;

$X_1$, $Y_1$, $R_1$ and $R_2$ individually are selected from the group consisting of H, linear or branched $C_1$–$C_{10}$ alkyl, linear or branched $C_1$–$C_{10}$ ester, linear or branched $C_1$–$C_{10}$ ketone, linear or branched $C_1$–$C_{10}$ carboxylic acid and linear or branched $C_1$–$C_{10}$ acetal, wherein at least one of $X_1$ and $Y_1$ are —COOR' wherein R' is an acid labile group;

$R_3$, $R_4$, $R_5$ and $R_6$ individually represent H or $CH_3$;

$R_7$ is an acid labile group.

The acid labile protecting group can be any of known protective groups which prevent the compound from dissolving in an alkaline developing solution. However, under the presence of acid, the acid labile group is substituted with acid, thereby making the compound soluble to the alkaline solution.

Some of conventional acid labile protecting groups are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0 789 278 (Aug. 13, 1997), U.S. Pat. No. 6,132,926 (Oct. 17, 2000), U.S. Pat. No. 6,180,316 B1 (Jan. 30, 2001), U.S. Pat. No. 6,225,020 B1 (May 1, 2001), U.S. Pat. No. 6,235,448 B1 (May 22, 2001) and U.S. Pat. No. 6,235,447 B1 (May 22, 2001). Preferably, acid labile protecting groups are selected from the group consisting of tert-butyl, 2,3,3-trimethylbutyl, 2-methyl 2-adamantyl, 2-ethyl 2-adamantyl, 8-ethyl 8-tricyclodecanyl, tetrahydropyran-2-yl, 2-methyl tetrahydropyran-2-yl, tetrahydrofuran-2-yl, 2-methyl tetrahydrofuran-2-yl, 1-methoxypropyl, 1-methoxy-1-methylethyl, 1-ethoxypropyl, 1-ethoxy-1-methylethyl, 1-methoxyethyl, 1-ethoxyethyl, tert-butoxyethyl, 1-isobutoxyethyl and 2-acetylmenth-1-yl.

In addition, the photoresist copolymer further comprises at least one repeating units of the following Formula 8 or Formula 9 in order to improve adhesiveness to the substrate and yield of polymerization.

Formula 8

[structure with $R_{10}$, $R_{11}$, $A_3$, $B_3$, $k_3$, $R_8$, $R_9$, $X_2$, $Y_2$]

wherein, $A_3$ and $B_3$ individually are selected from the group consisting of $CH_2$, $CH_2CH_2$, O or S;

$k_3$ is an integer ranging from 0 to 5;

$X_2$, $Y_2$, $R_8$ and $R_9$ individually are selected from the group consisting of H, linear or branched $C_1-C_{10}$ alkyl, linear or branched $C_1-C_{10}$ ester, linear or branched $C_1-C_{10}$ ketone, linear or branched $C_1-C_{10}$ carboxylic acid and linear or branched $C_1-C_{10}$ acetal, wherein at least one of $X_2$ and $Y_2$ are —COOR" (wherein R" is hydroxy alkyl); and $R_{10}$ and $R_{11}$ individually represent H or $CH_3$.

Formula 9

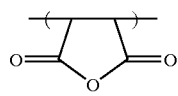

The above photoresist copolymers are preferably selected from the group consisting of Formulas 10a to 10g:

Formula 10a

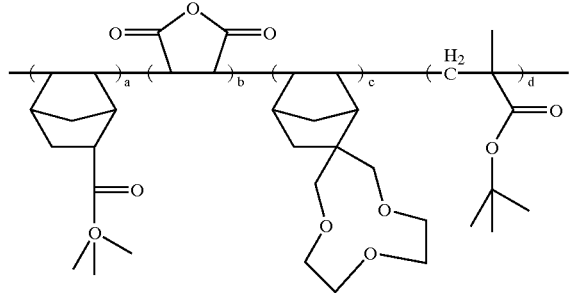

wherein, the ratio a+d:b:c=20–98 mol %: 0–60 mol %: 0.1–20 mol %;

Formula 10b

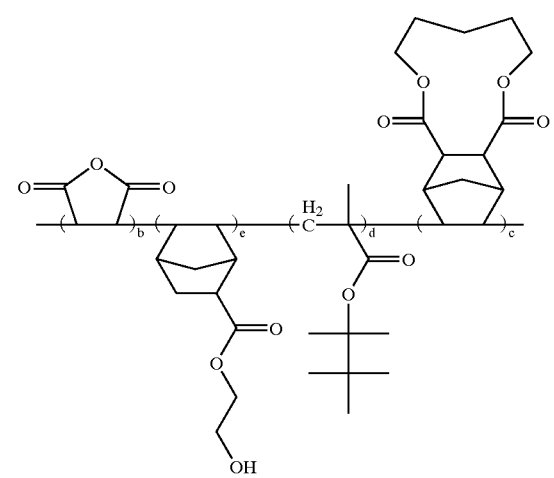

wherein, the ratio a+d:b:c=20–98 mol %: 0–60 mol %: 0.1–20 mol %;

Formula 10c

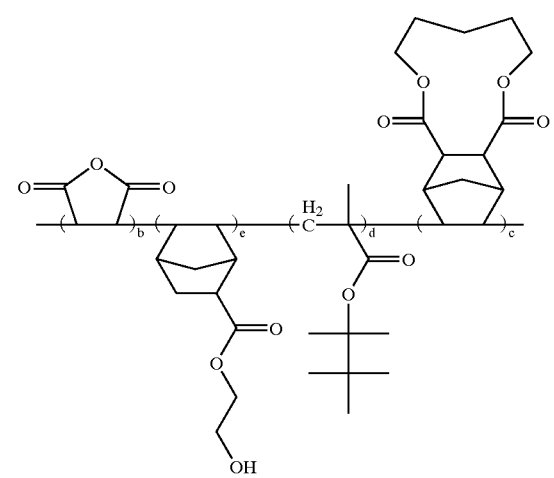

wherein, the ratio b:c:d:e=0–60 mol %: 0.1–20 mol %: 1–98 mol %: 0–49 mol %;

Formula 10d

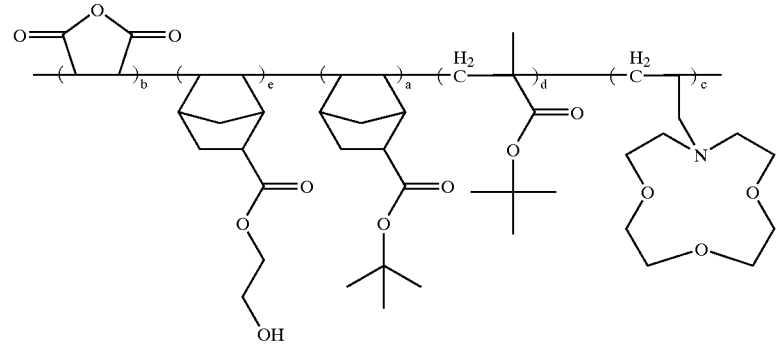

wherein, the ratio a+d:b:c:e=1–98 mol %: 0–60 mol %: 0.1–20 mol %: 0–49 mol %;

Formula 10e

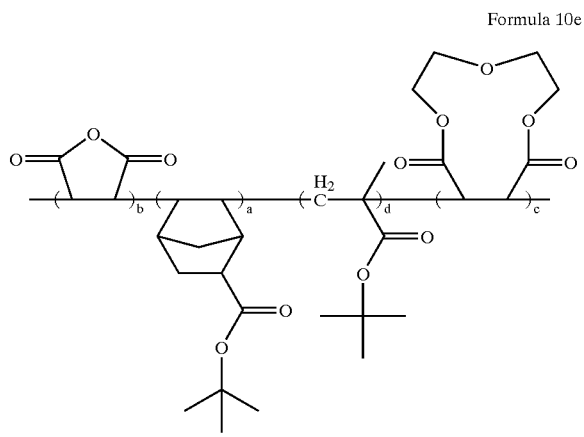

wherein, the ratio a+d:b:c=20–98 mol %: 0–60 mol %: 0.1–20 mol %;

Formula 10f

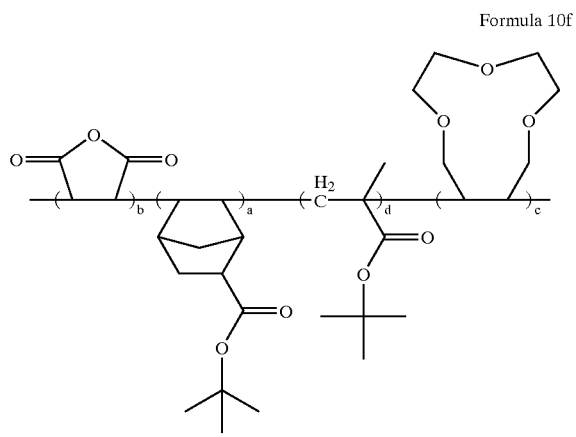

wherein, the ratio a+d:b:c=20–98 mol %: 0–60 mol %: 0.1–20 mol %; and

Formula 10g

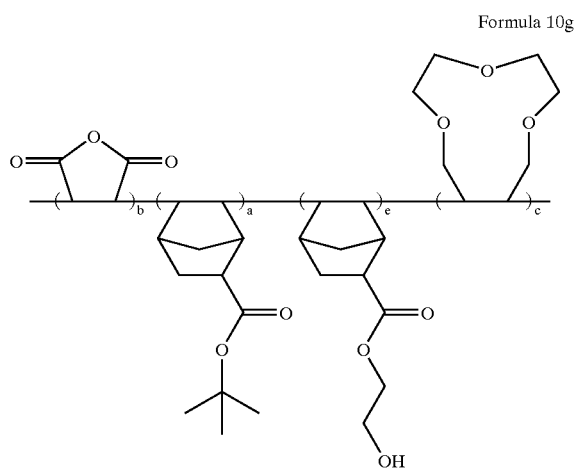

wherein, the ratio a:b:c:e=1–98 mol %: 0–60 mol %: 0.1–20 mol %: 0–49 mol %.

The photoresist copolymer comprises the above repeating unit in the main chain and can further comprise other comonomers or additives if necessary.

In addition, a photoresist composition is disclosed that comprises (i) a chemical amplification type photoresist copolymer comprising repeating unit of multi-oxygen-containing compound described above; (ii) a photoacid generator; and (iii) an organic solvent.

In particular, the disclosed photoresist copolymer is suitable for preparing a photoresist composition used in a lithography process employing a light source of extremely short wavelength of 250 nm or less.

As mentioned above, the photoresist composition can be prepared by mixing photoresist copolymer comprising the repeating unit of multi-oxygen-containing compound with photoacid generator and organic solvent. In addition, it can be prepared by adding multi-oxygen-containing compound directly into the photoresist composition comprising conventional chemical amplification type photoresist copolymer.

Any of conventional photoacid generator, which is able to generate acids when it is exposed to light, can be used. Some of conventional photoacid generators are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997), U.S. Pat. No. 6,132,926 (Oct. 17, 2000), U.S. Pat. No. 6,143,463 (Nov. 7, 2000), U.S. Pat. No. 6,150,069 (Nov. 21, 2000), U.S. Pat. No. 6,180,316 B1 (Jan. 30, 2001), U.S. Pat. No. 6,225,020 B1 (May 1, 2001), U.S. Pat. No. 6,235,448 B1(May 22, 2001) and U.S. Pat. No. 6,235,447 B1 (May 22, 2001). Sulfide type or onium type compounds are primarily used for the photoacid generator.

More preferred photoacid generators are selected from the group consisting of diphenyl iodide hexafluorophosphate, diphenyl iodide hexafluoroarsenate, diphenyl iodide hexafluoroantimonate, diphenyl p-methoxyphenylsulfonium triflate, diphenyl p-toluenylsulfonium triflate, diphenyl p-isobutylphenylsulfonium triflate, diphenyl p-tert-butylphenylsulfonium triflate , triphenylsulfonium hexafluorophosphate, triphenylsulfonium hexafluoroarsenate, triphenylsulfonium hexafluoroantimonate, triphenylsulfonium triflate, dibutylnaphthylsulfonium triflate, phthalimidotrifluoromethane sulfonate, dinitrobenzyltosylate, n-decyl disulfone, naphthylimido trifluoromethane sulfonate and mixtures thereof.

Typically, the amount of photoacid generator ranges from about 0.01 to about 10% by weight of the photoresist copolymer employed. It has been found that when the photoacid generator is used in the amount less than about 0.01%, it lowers photosensitivity of the photoresist composition, and when the photoacid generator is used in the amount greater than about 10%, it results in a poor pattern formation due to its high absorption.

On the other hand, any of conventional organic solvent can be employed on generating the photoresist composition and some of the conventional solvents are also disclosed in the documents described above. Preferred organic solvents for the photoresist composition include methyl 3-methoxypropionate, ethyl 3-ethoxypropionate, propylene glycol methyl ether acetate, cyclohexanone, 2-heptanone, ethyl lactate, γ-butyrolactone or mixtures thereof.

The amount of organic solvent ranges from about 500 to about 2000% by weight of the photoresist polymer to coat the photoresist in a wanted thickness.

Processes for forming a photoresist pattern comprise the steps of:

(a) coating the photoresist composition described above on a wafer to form a photoresist film;

(b) exposing the photoresist film to light using an exposer; and (c) developing the exposed photoresist film to obtain a photoresist pattern.

The process for forming the photoresist pattern can further include a soft baking which is performed before part (b) and/or a post baking step which is performed after part (b). Preferably, the soft and post baking steps are performed at temperature ranging from about 70 to about 200° C.

Exemplary light sources which are useful for forming the photoresist pattern include ArF, KrF, E-beam, EUV, ion beam or X-ray. Preferably, the irradiation energy in part (b) is in the range from about 1 mJ/cm$^2$ and about 100 mJ/cm$^2$.

On the other hand, part (c) can be performed in alkaline developing solution which is preferably TMAH aqueous solution of 0.01 to 5 wt. %.

To explain in more detail, the photoresist composition according to the present invention is coated on silicon wafer as the underlying layer to form a photoresist thin film and soft-baked at a temperature ranging from about 80–150° C. for a time period ranging from about 1 to about 5 minutes in an oven or a hot plate. After soft-baking, the photoresist thin film is exposed using an exposer and post-baked at a temperature ranging from about 100 to about 200° C.

In addition, a semiconductor device manufactured using the photoresist composition described above is also disclosed.

The disclosed photoresist monomers, copolymers and compositions will now be described in more details by referring to examples below, which are not intended to be limiting.

I. Preparation of Photoresist Monomers

EXAMPLE 1

Synthesis of Compound of Formula 3a

To 500 mL of anhydrous tetrahydrofuran was added 5-norbornene-2,2-dimethanol(0.1 mole) and di(ethyleneglycol)di-p-tosylate(0.1 mole). The resulting solution was slowly added into the 2 L of 3-neck flask having LiOH(0.21 mole), and the resulting solution was reacted at room temperature for about 24 hours.

Thereafter, the resulting mixture was distilled to remove the solvent, and the residual mixture was extracted in 1 L of ethyl acetate. Then the layer of ethyl acetate was washed with water several times, dehydrated, filtered and distilled, thereby obtaining the compound of Formula 3a (yield: 54%).

EXAMPLE 2

Synthesis of Compound of Formula 3b

To 500 mL of anhydrous tetrahydrofuran was added 5-norbornene-2,3-dimethanol(0.1 mole) and di(ethyleneglycol)di-p-tosylate(0.1 mole). The resulting solution was slowly added into the 2 L of 3-neck flask having LiOH(0.21 mole), and the resulting solution was reacted at room temperature for about 24 hours.

Thereafter, the resulting mixture was distilled to remove the solvent, and the residual mixture was extracted in 1 L of ethyl acetate. Then the layer of ethyl acetate was washed with water several times, dehydrated, filtered and distilled, thereby obtaining the compound of Formula 3b (yield: 62%).

EXAMPLE 3

Synthesis of Compound of Formula 3c

To 500 mL of anhydrous tetrahydrofuran was added 3,6-endomethylene-1,2,3,6-tetrahydrophthaloyl chloride (0.1 mole) and di(ethyleneglycol) (0.1 mole). The resulting solution was slowly added into the 2 L of 3-neck flask having LiOH(0.21 mole) and triethylamine(0.2 mole), and the resulting solution was reacted at room temperature for about 24 hours.

Thereafter, the solid was filtered off, the resulting mixture was distilled to remove the solvent, and the residual mixture was extracted in 1 L of ethyl acetate. Then the layer of ethyl acetate was washed with water several times, dehydrated, filtered and distilled, thereby obtaining the compound of Formula 3c (yield: 74%).

EXAMPLE 4

Synthesis of Compound of Formula 3d

To 500 mL of anhydrous tetrahydrofuran was added allylamine(0.1 mole) and sodium carbonate(0.2 mole). A solution obtained by dissolving tetra(ethyleneglycol)-di-p-tosylate(0.1 mole) in 500 mL anhydrous tetrahydrofuran was slowly added thereto, and the resulting solution was reacted at room temperature for about 24 hours.

Thereafter, the resulting mixture was distilled to remove the solvent, and 300 mL water was added to the residual mixture and the resultant was extracted in 1 L of ethyl acetate. Then the layer of ethyl acetate was washed with water several times, dehydrated, filtered and distilled, thereby obtaining the compound of Formula 3d, N-allyl-4-aza-12-crown-4 (yield: 43%).

EXAMPLE 5

Synthesis of Compound of Formula 3e

To 500 mL of anhydrous tetrahydrofuran was added fumaryl chloride (0.1 mole) and di(ethyleneglycol)(0.1 mole). The resulting solution was slowly added into the 2 L of 3-neck flask having LiOH(0.01 mole) and triethylamine (0.2 mole), and the resulting solution was reacted at room temperature for about 24 hours.

Thereafter, the solid was filtered off, the resulting mixture was distilled to remove the solvent, and the residual mixture was extracted in 1 L of ethyl acetate. Then the layer of ethyl acetate was washed with water several times, dehydrated, filtered and distilled, thereby obtaining the compound of Formula 3e (yield : 78%).

EXAMPLE 6

Synthesis of Compound of Formula 3f

To 500 mL of anhydrous tetrahydrofuran was added 2-butene-1,4-diol (0.1 mole) and di(ethyleneglycol)di-p-tosylate(0.1 mole). The resulting solution was slowly added into the 2 L of 3-neck flask having LiOH(0.21 mole), and the resulting solution was reacted at room temperature for about 24 hours.

Thereafter, the resulting mixture was distilled to remove the solvent, and the residual mixture was extracted in 1 L of ethyl acetate. Then the layer of ethyl acetate was washed with water several times, dehydrated, filtered and distilled, thereby obtaining the compound of Formula 3f (yield: 63%).

II. Preparation of Photoresist Copolymers

EXAMPLE 7

Preparation of Photoresist Copolymer of Formula 10a

To 10 mL of anhydrous tetrahydrofuran was added tert-butyl bicyclo[2,2,1]hept-5-ene-2-carboxylate(0.03 mole), the compound of Formula 3a obtained from Example 1(0.01 mole), tert-butyl methacrylate(0.02 mole), maleic anhydride (0.031 mol) and AIBN(0.05 g), and the resulting solution was reacted at about 67° C. for about 12 hours. Thereafter, a polymer was precipitated and filtered in petroleum ether solution, thereby obtaining the polymer of Formula 10a (yield : 48%).

EXAMPLE 8

Preparation of Photoresist Copolymer of Formula 10b

To 10 mL of anhydrous tetrahydrofuran was added tert-butyl bicyclo[2,2,1]hept-5-ene-2-carboxylate(0.02 mole), the compound of Formula 3b obtained from Example 2(0.01 mole), methyl adamantyl methacrylate(0.02 mole), maleic anhydride(0.021 mol) and AIBN(0.05 g), and the resulting solution was reacted at about 67° C. for about 12 hours. Thereafter, a polymer was precipitated and filtered in petroleum ether solution, thereby obtaining the polymer of Formula 10b (yield: 52%).

EXAMPLE 9

Preparation of Photoresist Copolymer of Formula 10c

To 20 mL of anhydrous tetrahydrofuran was added 2-hydroxyethyl bicyclo[2,2,1]hept-5-ene-2-carboxylate (0.02 mole), the compound of Formula 3c obtained from Example 3(0.001 mole), 2,3,3-trimethylbutyl 2-methacrylate(0.03 mole), maleic anhydride(0.021 mol) and AIBN(0.05 g), and the resulting solution was reacted at about 67° C. for about 12 hours. Thereafter, a polymer was precipitated and filtered in methanol/water solution, thereby obtaining the polymer of Formula 10c (yield: 62%).

EXAMPLE 10

Preparation of Photoresist Copolymer of Formula 10d

To 10 mL of anhydrous tetrahydrofuran was added 2-hydroxyethyl bicyclo[2,2,1]hept-5-ene-2-carboxylate (0.01 mole), tert-butyl bicyclo[2,2,1]hept-5-ene-2-carboxylate(0.02 mole), the compound of Formula 3d obtained from Example 4(0.0005 mole), tert-butyl methacrylate(0.02 mole), maleic anhydride(0.0305 mol) and AIBN(0.05 g), and the resulting solution was reacted at about 67° C. for about 12 hours. Thereafter, a polymer was precipitated and filtered in petroleum ether solution, thereby obtaining the polymer of Formula 10d (yield: 42%).

EXAMPLE 11

Preparation of Photoresist Copolymer of Formula 10e

To 10 mL of anhydrous tetrahydrofuran was added tert-butyl bicyclo[2,2,1]hept-5-ene-2-carboxylate(0.02 mole), the compound of Formula 3e obtained from Example 5(0.001 mole), tert-butyl methacrylate(0.02 mole), maleic anhydride(0.021 mol) and AIBN(0.05 g), and the resulting solution was reacted at about 67° C. for about 12 hours. Thereafter, a polymer was precipitated and filtered in petroleum ether solution, thereby obtaining the polymer of Formula 10e (yield : 47%).

EXAMPLE 12

Preparation of Photoresist Copolymer of Formula 10f

To 10 mL of anhydrous tetrahydrofuran was added tert-butyl bicyclo[2,2,1]hept-5-ene-2-carboxylate(0.02 mole), the compound of Formula 3f obtained from Example 6(0.001 mole), tert-butyl methacrylate(0.02 mole), maleic anhydride(0.021 mol) and AIBN(0.05 g), and the resulting solution was reacted at about 67° C. for about 12 hours. Thereafter, a polymer was precipitated and filtered in petroleum ether solution, thereby obtaining the polymer of Formula 10f (yield: 45%).

EXAMPLE 13

Preparation of Photoresist Copolymer of Formula 10g

To 10 mL of anhydrous tetrahydrofuran was added tert-butyl bicyclo[2,2,1]hept-5-ene-2-carboxylate(0.02 mole), the compound of Formula 3f obtained from Example 6(0.001 mole), 2-hydroxyethyl bicyclo[2,2,1]hept-5-ene-2-carboxylate(0.02 mole), maleic anhydride(0.041 mol) and AIBN(0.05 g), and the resulting solution was reacted at about 67° C. for about 12 hours. Thereafter, a polymer was precipitated and filtered in petroleum ether solution, thereby obtaining the polymer of Formula 10g (yield: 51%).

III. Preparation of Photoresist Compositions and Formation of Patterns

EXAMPLE 14

Preparation of Photoresist Compositions and Formation of Patterns(1)

To 25 g of ethyl 3-ethoxypropionate was added 4 g of the photoresist polymer obtained from Example 7, 0.04 g of triphenylsulfonium triflate as a photoacid generator. The polymer was precipitated and filtered in 0.201 $\mu$m filter to obtain a photoresist composition.

The photoresist composition thus prepared was spin-coated on silicon wafer to form a photoresist film, and soft-baked at about 110° C. for about 90 seconds. After baking, the photoresist was exposed to light using a ArF laser exposer, and then post-baked at about 110° C. for about 90 seconds. When the post-baking was completed, it was developed in 2.38 wt. % aqueous TMAH solution for 40 seconds, to obtain 0.11 $\mu$m L/S pattern (see FIG. 1).

EXAMPLE 15

Preparation of Photoresist Compositions and Formation of Patterns(2)

Figure 2:
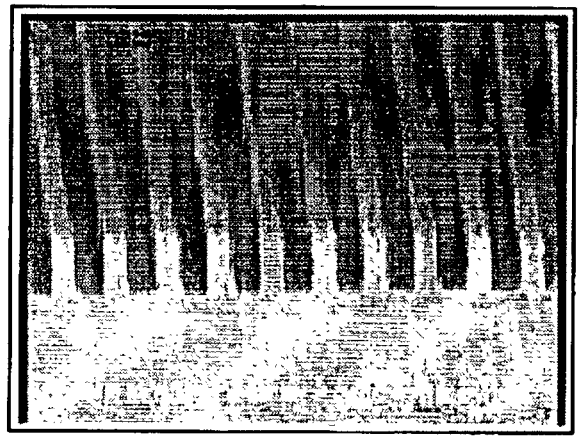
FIG. 2 is a photograph of a photoresist pattern obtained from Example 15.

The procedure of Example 14 was repeated using the polymer of Example 8 instead of the polymer of Example 7 to obtain the pattern of 0.11 $\mu$m L/S pattern (see FIG. 2).

EXAMPLE 16

Preparation of Photoresist Compositions and Formation of Patterns(3)

Figure 3:
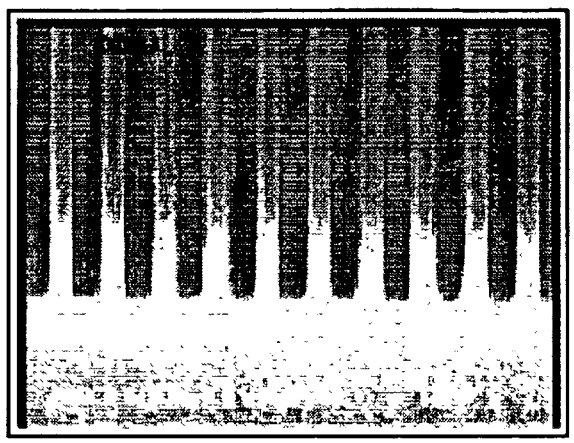
FIG. 3 is a photograph of a photoresist pattern obtained from Example 16.

The procedure of Example 14 was repeated using the polymer of Example 9 instead of the polymer of Example 7 to obtain the pattern of 0.11 $\mu$m L/S pattern (see FIG. 3).

EXAMPLE 17

Preparation of Photoresist Compositions and Formation of Patterns(4)

Figure 4:
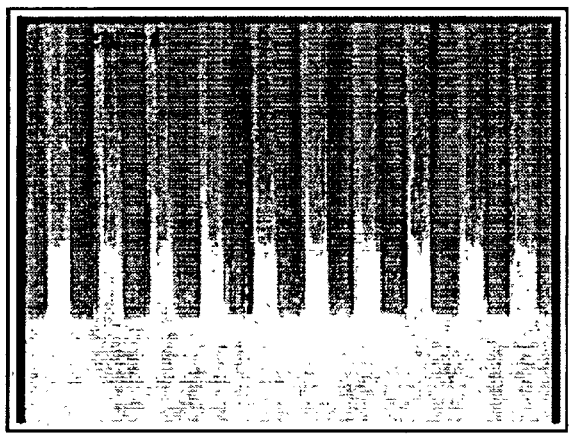
FIG. 4 is a photograph of a photoresist pattern obtained from Example 17.

The procedure of Example 14 was repeated using the polymer of Example 10 instead of the polymer of Example 7 to obtain the pattern of 0.11 $\mu$m L/S pattern (see FIG. 4).

EXAMPLE 18

Preparation of Photoresist Compositions and Formation of Patterns(5)

Figure 5:
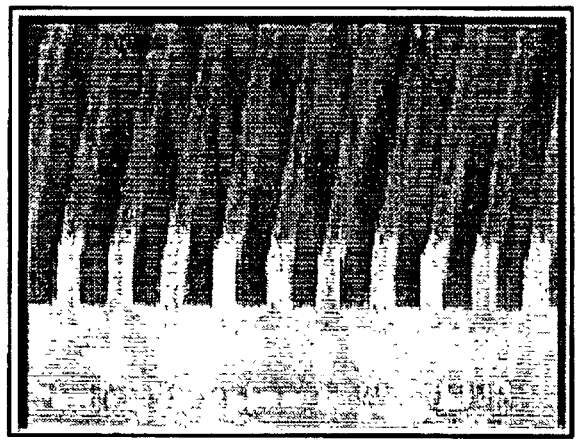
FIG. 5 is a photograph of a photoresist pattern obtained from Example 18.

The procedure of Example 14 was repeated using the polymer of Example 11 instead of the polymer of Example 7 to obtain the pattern of 0.11 μm L/S pattern (see FIG. 5).

EXAMPLE 19

Preparation of Photoresist Compositions and Formation of Patterns(6)

Figure 6:
FIG. 6 is a photograph of a photoresist pattern obtained from Example 19.

The procedure of Example 14 was repeated using the polymer of Example 12 instead of the polymer of Example 7 to obtain the pattern of 0.11 μm L/S pattern (see FIG. 6).

EXAMPLE 20

Preparation of Photoresist Compositions and Formation of Patterns(7)

Figure 7:
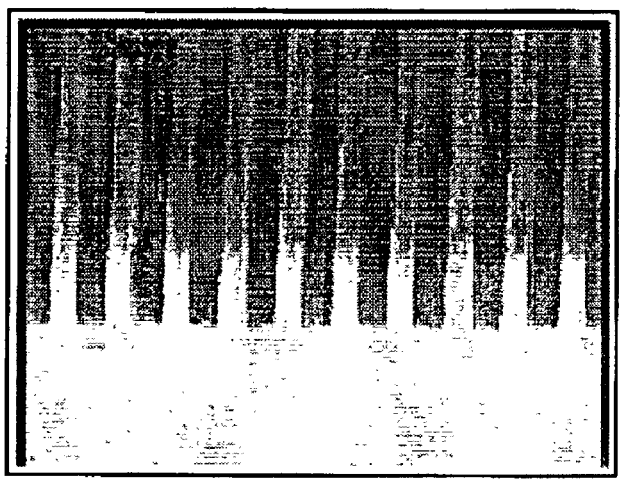
FIG. 7 is a photograph of a photoresist pattern obtained from Example 20.

The procedure of Example 14 was repeated using the polymer of Example 13 instead of the polymer of Example 7 to obtain the pattern of 0.11 μm L/S pattern (see FIG. 7).

As discussed earlier, the line edge roughness and slop of pattern are improved when ultrafine photoresist pattern is formed by adding the photoresist copolymer comprising multi-oxygen-containing compound as a repeating unit, wherein the compound comprises ethyleneoxy moiety and has at least one polymerizable carbon-carbon double bonds, into the photoresist composition. In addition, the shape of pattern is improved by eliminating top loss and the adhesion of pattern to the substrate is improved.

What is claimed:

1. A photoresist monomer selected from the group consisting of Formulas 2a, 2b, 2c, 2d and 2f:

Formula 2a wherein $n^a$ for Formula 2a is an integer ranging from 1 to 5;

Formula 2b wherein $n^b$ for Formula 2b is an integer ranging from 1 to 5;

Formula 2c wherein $n^c$ for Formula 2c is an integer ranging from 1 to 5;

Formula 2d wherein $n^d$ for Formula 2d is an integer ranging from 1 to 5;
wherein X is N or CH; and Formula 2f wherein $n^f$ for Formula 2f is 1 or 4.

2. The photoresist monomer according to claim 1, wherein the monomer is selected from the group consisting of Formulas 3a, 3b, 3c, 3d and 3f:

Formula 3a

Formula 3b

Formula 3c

Formula 3d

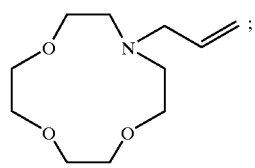

and

Formula 3f

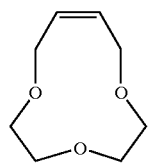

3. A photoresist polymer comprising a photoresist monomer of claim 2.

4. A photoresist polymer comprising:

a photoresist monomer of claim 1.

5. The photoresist polymer according to claim 4, wherein polymer comprises a repeating unit is selected from the group consisting of Formulas 4a, 4b, 4c, 4d and 4f:

Formula 4a

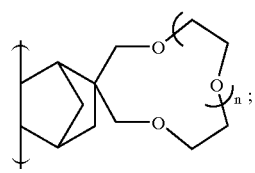

wherein $n^a$ for Formula 4a is an integer ranging from 1 to 5;

Formula 4b

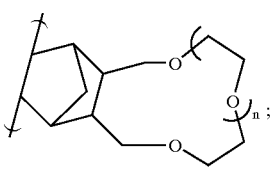

wherein $n^b$ for Formula 4b is an integer ranging from 1 to 5;

Formula 4c

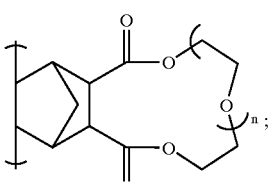

wherein $n^c$ for Formula 4c is an integer ranging from 1 to 5;

Formula 4d

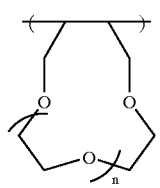

wherein $n^d$ for Formula 4d is an integer ranging from 1 to 5 wherein X is N or CH;

Formula 4f

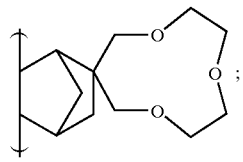

wherein $n^f$ for Formula 4f is 1 to 4.

6. The photoresist polymer according to claim 5, wherein the repeating unit is selected from the group consisting of Formulas 5a, 5b, 5c, 5d and to 5f:

Formula 5a

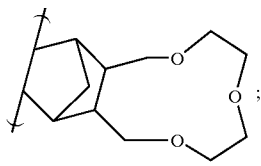

Formula 5b

Formula 5c

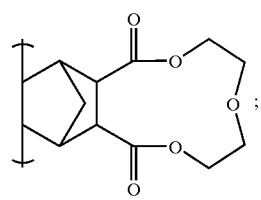

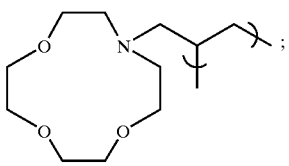

Formula 5d and

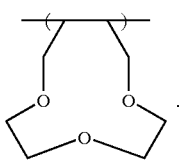

Formula 5f

7. The photoresist polymer according to claim 4, wherein the polymer further comprises at least one repeating unit represented by Formula 6 or Formula 7:

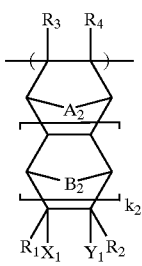

Formula 6

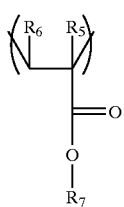

Formula 7 wherein
$A_2$ and $B_2$ individually are selected from the group consisting of $CH_2$, $CH_2CH_2$, O or S;
$k_2$ is an integer from 0 to 5;
$X_1$, $Y_1$, $R_1$ and $R_2$ individually are selected from the group consisting of H, linear $C_1$–$C_{10}$ alkyl, branched $C_1$–$C_{10}$ alkyl, linear $C_1$–$C_{10}$ ester, branched $C_1$–$C_{10}$ ester, linear branched $C_1$–$C_{10}$ ketone, linear $C_1$–$C_{10}$ carboxylic acid, branched $C_1$–$C_{10}$ carboxylic acid, linear $C_1$–$C_{10}$ acetal, and branched $C_1$–$C_{10}$ acetal, wherein at least one of $X_1$ and $Y_1$ are —COOR' wherein R' is an acid labile group;
$R_3$, $R_4$, $R_5$ and $R_6$ individually are H or $CH_3$; and
$R_7$ is an acid labile group.

8. The photoresist polymer according to claim 7, wherein the polymer further comprises at least one repeating unit represented by following Formula 9 or Formula 9:

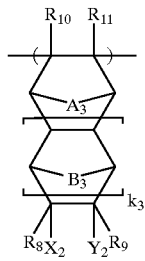

Formula 8 wherein
$A_3$ and $B_3$ individually are selected from the group consisting of $CH_2$, $CH_2CH_2$, O and S;
$k_3$ is an integer ranging from 0 to 5;
$X_2$, $Y_2$, $R_8$ and $R_9$ individually are selected from the group consisting of H, linear $C_1$–$C_{10}$ alkyl, branched $C_1$–$C_{10}$ alkyl, linear $C_1$–$C_{10}$ ester, branched $C_1$–$C_{10}$ ester, linear $C_1$–$C_{10}$ ketone, branched $C_1$–$C_{10}$ ketone, linear $C_1$–$C_{10}$ carboxylic acid, branched $C_1$–$C_{10}$ carboxylic acid, linear $C_1$–$C_{10}$ acetal, and branched $C_1$–$C_{10}$ acetal, wherein at least one of $X_2$ and $Y_2$ are —COOR" wherein R" is hydroxy alkyl; and
$R_{10}$ and $R_{11}$ individually represent H or $CH_3$;

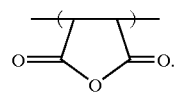

Formula 9

9. The photoresist polymer according to claim 7, wherein the polymer is selected from the group consisting of Formulas 10a, 10b, 10c, 10d, 10f and 10g:

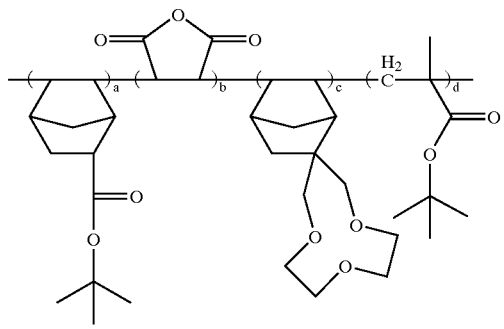

Formula 10a wherein a+d:b:c=20–98 mol %: 0–60 mol %: 0.1–20 mol %;

Formula 10b

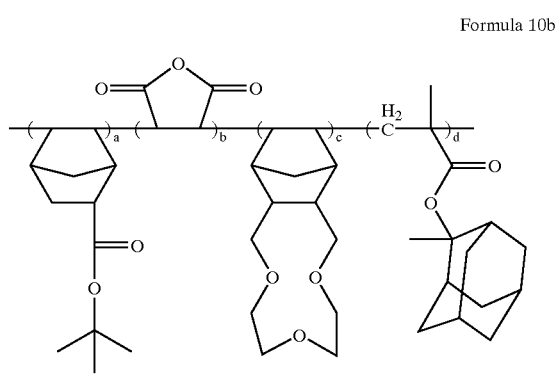

wherein a+d:b:c=20–98 mol %: 0–60 mol %: 0.1–20 mol %;

Formula 10c

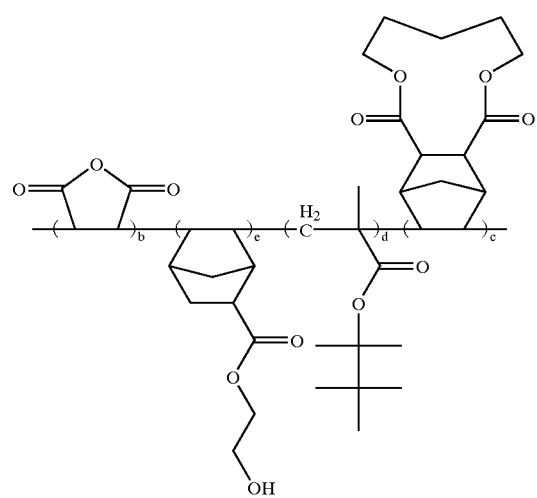

wherein b:c:d:e=0–60 mol %: 0.1–20 mol %: 1–98 mol %: 0–49 mol %;

Formula 10d

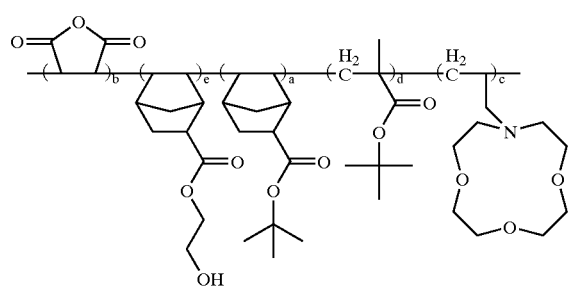

wherein a+d:b:c:e=1–98 mol %: 0–60 mol %: 0.1–20 mol %: 0–49 mol %;

Formula 10f

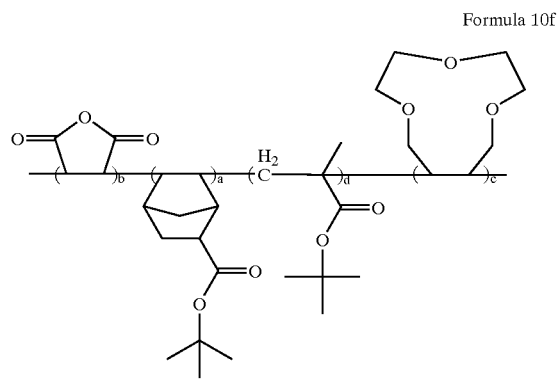

wherein a+d:b:c20–98 mol %: 0–60 mol %: 0.1–20 mol %; and

Formula 10g

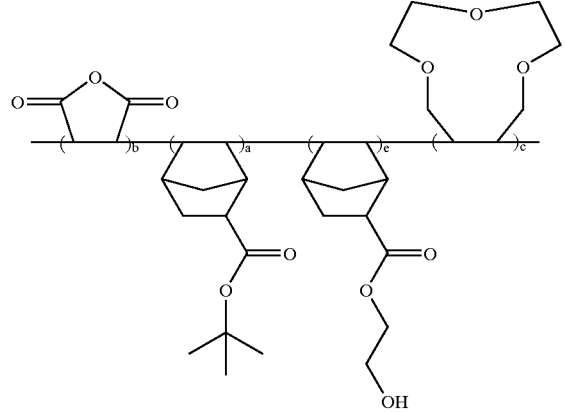

wherein a:b:c:e=1–98 mol %: 0–60 mol %: 0.1–20 mol %: 0–49 mol %.

10. A photoresist composition comprising:
(i) a photoresist polymer of claim 4;
(ii) an organic solvent; and
(iii) a photoacid generator.

11. The photoresist composition according to claim 10, wherein the photoacid generator is selected from the group consisting of diphenyl iodide hexafluorophosphate, diphenyl iodide hexafluoroarsenate, diphenyl iodide hexafluoroantimonate, diphenyl p-methoxyphenylsulfonium triflate, diphenyl p-toluenylsulfonium triflate, diphenyl p-isobutylphenylsulfonium triflate, diphenyl p-tert-butylphenylsulfonium triflate, triphenylsulfonium hexafluorophosphate, triphenylsulfonium hexafluoroarsenate, triphenylsulfonium hexafluoroantimonate, triphenylsulfonium triflate, dibutyl-naphthylsulfonium triflate, phthalimidotrifluoromethane sulfonate, dinitrobenzyltosylate, n-decyl disulfone, naphthylimido trifluoromethane sulfonate and mixtures thereof.

12. The photoresist composition according to claim 10, wherein the organic solvent is selected from the group consisting of methyl 3-methoxypropionate, ethyl 3-ethoxypropionate, propylene glycol methyl ether acetate, cyclohexanone, 2-heptanone, ethyl lactate, γ-butyrolactone and mixtures thereof.

13. A process for forming a photoresist pattern, comprising:

(a) coating the photoresist composition of claim 10 on a wafer to form a photoresist film;

(b) exposing the photoresist film to light; and (c) developing the exposed photoresist film to obtain a photoresist pattern.

14. The process according to claim 13, further comprising soft baking before part (b) and/or post baking after part (b).

15. The process according to claim 14, wherein the soft and post bakings are individually performed at a temperature ranging from about 50 to about 200° C.

16. The process according to claim 13, wherein the light is selected from the group consisting of VUV (157 nm), ArF (193 nm), KrF (248 nm), E-beam, EUV (13 nm) and ion beam.

17. A semiconductor element manufactured according to the process of claim 13.

* * * * *

UNITED STATES PATENT AND TRADEMARK OFFICE
CERTIFICATE OF CORRECTION

PATENT NO. : 6,924,078 B2  Page 1 of 4
DATED : August 2, 2005
INVENTOR(S) : Lee et al.

It is certified that error appears in the above-identified patent and that said Letters Patent is hereby corrected as shown below:

Column 17,
Formula 2a, change "n" to -- $n^a$ -- as shown below:

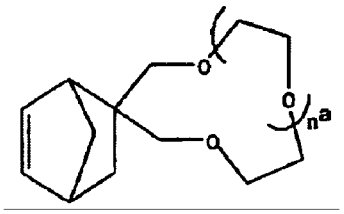

Formula 2b, change "n" to -- $n^b$ -- as shown below:

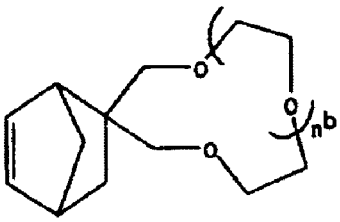

Column 18,
Formula 2c, change "n" to -- $n^c$ -- as shown below:

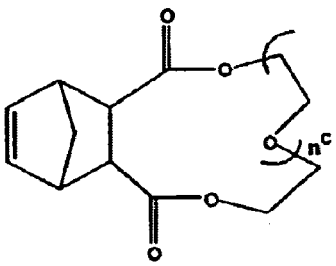

Formula 2d, change "n" to -- $n^d$ -- as shown below:

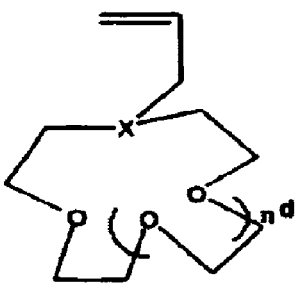

UNITED STATES PATENT AND TRADEMARK OFFICE
CERTIFICATE OF CORRECTION

PATENT NO. : 6,924,078 B2
DATED : August 2, 2005
INVENTOR(S) : Lee et al.

It is certified that error appears in the above-identified patent and that said Letters Patent is hereby corrected as shown below:

Column 18 (cont'd),
Formula 2f, change "n" to -- $n^f$ -- as shown below:

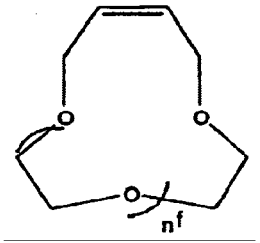

Column 19,
Formula 4a, change "n" to -- $n^a$ -- as shown below:

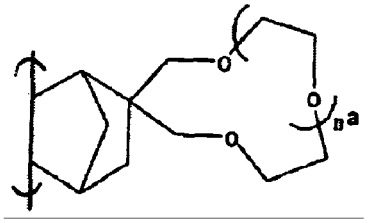

Formula 4b, change "n" to -- $n^b$ -- as shown below:

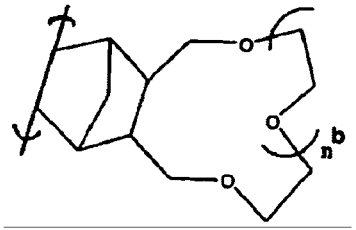

Formula 4c, change "n" to -- $n^c$ -- as shown below:

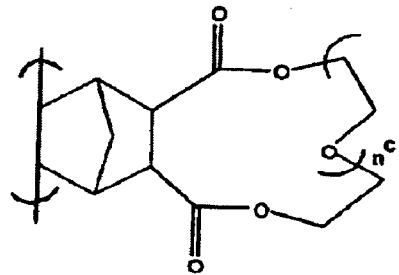

UNITED STATES PATENT AND TRADEMARK OFFICE
CERTIFICATE OF CORRECTION

PATENT NO.   : 6,924,078 B2
DATED         : August 2, 2005
INVENTOR(S)  : Lee et al.

It is certified that error appears in the above-identified patent and that said Letters Patent is hereby corrected as shown below:

Column 20,
Formula 4d, change "n" to -- $n^d$ -- as shown below:

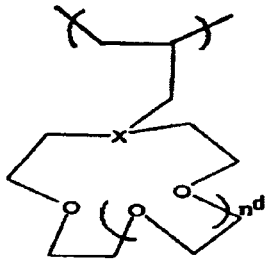

Formula 4f, change "n" to -- $n^f$ -- as shown below:

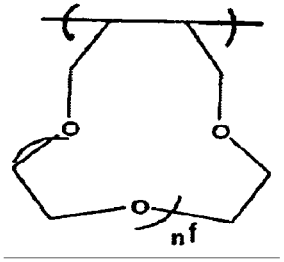

Column 20,
Line 33, delete "and to 5f" and insert -- and 5f --.

Column 21,
Line 64, delete "are" and insert -- is --.

Column 22,
Line 33, delete "are" and insert -- is --.

UNITED STATES PATENT AND TRADEMARK OFFICE
CERTIFICATE OF CORRECTION

PATENT NO.   : 6,924,078 B2
DATED        : August 2, 2005
INVENTOR(S)  : Lee et al.

It is certified that error appears in the above-identified patent and that said Letters Patent is hereby corrected as shown below:

Column 24,
Line 18, delete "c20-98" and insert -- c = 20-98 --.

Signed and Sealed this

Seventh Day of March, 2006

JON W. DUDAS
*Director of the United States Patent and Trademark Office*

UNITED STATES PATENT AND TRADEMARK OFFICE
CERTIFICATE OF CORRECTION

PATENT NO.       : 6,924,078 B2
APPLICATION NO.  : 10/225992
DATED            : August 2, 2005
INVENTOR(S)      : Lee et al.

It is certified that error appears in the above-identified patent and that said Letters Patent is hereby corrected as shown below:

In the Claims:

In Claim 1, Column 17, Formula 2a, please change "n" to --$n^a$-- as shown below:

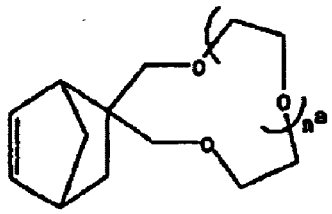

In Claim 1, Column 17, Formula 2b, please change "n" to --$n^b$-- as shown below:

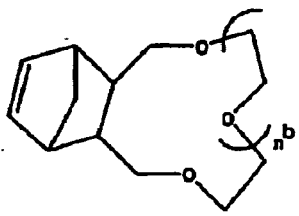

In Claim 1, Column 18, Formula 2c, please change "n" to --$n^c$-- as shown below:

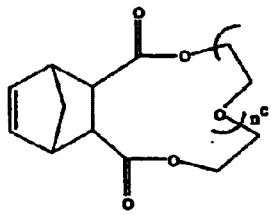

UNITED STATES PATENT AND TRADEMARK OFFICE
CERTIFICATE OF CORRECTION

PATENT NO.         : 6,924,078 B2
APPLICATION NO. : 10/225992
DATED              : August 2, 2005
INVENTOR(S)       : Lee et al.

It is certified that error appears in the above-identified patent and that said Letters Patent is hereby corrected as shown below:

In the Claims (cont'd):

In Claim 1, Column 18, Formula 2d, please change "n" to --$n^d$-- as shown below:

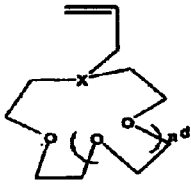

In Claim 1, Column 18, Formula 2f, please change "n" to --$n^f$-- as shown below:

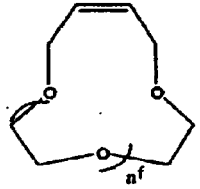

In Claim 5, Column 19, Formula 4a, please change "n" to --$n^a$-- as shown below:

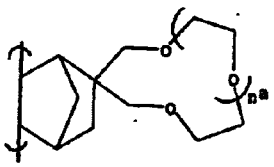

UNITED STATES PATENT AND TRADEMARK OFFICE
CERTIFICATE OF CORRECTION

PATENT NO.        : 6,924,078 B2
APPLICATION NO. : 10/225992
DATED               : August 2, 2005
INVENTOR(S)      : Lee et al.

It is certified that error appears in the above-identified patent and that said Letters Patent is hereby corrected as shown below:

In the Claims (cont'd):

In Claim 5, Column 19, Formula 4b, please change "n" to --$n^b$-- as shown below:

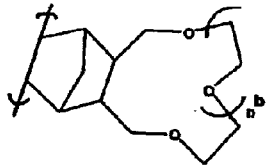

In Claim 5, Column 19, Formula 4c, please change "n" to --$n^c$-- as shown below:

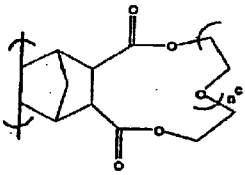

In Claim 5, Column 20, Formula 4d, please change "n" to --$n^d$-- as shown below:

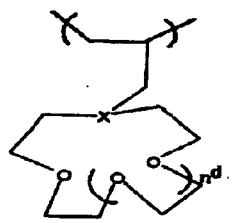

UNITED STATES PATENT AND TRADEMARK OFFICE
CERTIFICATE OF CORRECTION

PATENT NO. : 6,924,078 B2  
APPLICATION NO. : 10/225992  
DATED : August 2, 2005  
INVENTOR(S) : Lee et al.

It is certified that error appears in the above-identified patent and that said Letters Patent is hereby corrected as shown below:

In the Claims (cont'd):

In Claim 5, Column 20, Formula 4f, please cange "n" to --$n^f$-- as shown below:

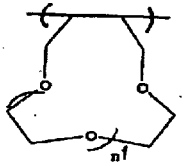

In Claim 5, Column 20, Line 33, please delete "and to 5f" and insert --and 5f--.

In Claim 7, Column 21, Line 64, please delete "are" and insert --is--.

In Claim 8, Column 22, Line 33, please delete "are" and insert --is--.

In Claim 9, Column 24, Line 18, please delete "c20-98" and insert --c = 20-98--.

This certificate supersedes Certificate of Correction issued March 7, 2006.

Signed and Sealed this

Seventeenth Day of October, 2006

JON W. DUDAS  
*Director of the United States Patent and Trademark Office*